US008428675B2

(12) United States Patent
McKenna (10) Patent No.: US 8,428,675 B2
(45) Date of Patent: Apr. 23, 2013

(54) NANOFIBER ADHESIVES USED IN MEDICAL DEVICES

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 905 days.

(21) Appl. No.: 12/543,920

(22) Filed: Aug. 19, 2009

(65) Prior Publication Data

US 2011/0046461 A1 Feb. 24, 2011

(51) Int. Cl.
*A61B 5/1455* (2006.01)

(52) U.S. Cl.
USPC .............. 600/323; 600/386; 600/391

(58) Field of Classification Search ........... 156/155, 156/152; 264/139; 600/323, 386, 391; 118/696; 428/365
See application file for complete search history.

(56) References Cited

U.S. PATENT DOCUMENTS

| | | | |
|---|---|---|---|
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,643,193 A * | 2/1987 | DeMarzo | 600/392 |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Kyoung-sik Moon et al, Nano-conductive Adhesives for Nano-electronics Interconnection, Springer Science and Business Media, 2010.*

(Continued)

*Primary Examiner* — Clayton E Laballe
*Assistant Examiner* — Kevin Butler
(74) *Attorney, Agent, or Firm* — Fletcher Yoder (57) ABSTRACT

Nanofiber adhesives and their uses with device, such as medical devices, are described. In one embodiment, a nanofiber adhesive layer may be disposed on a surface of a medical device, such as a backing layer of a sensor, for adhesion to a substrate. The nanofiber adhesive layer may allow durable adhesion to the substrate. Other described features may include materials and methods to determine the attachment of the medical device to a patient by determining the adhesive state of the adhesive layer.

18 Claims, 3 Drawing Sheets

U.S. PATENT DOCUMENTS

| | | | |
|---|---|---|---|
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,353 A * | 7/1989 | Engel | 600/391 |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A * | 11/1989 | Jaeb et al. | 356/41 |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A * | 10/1991 | Muz | 600/344 |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A * | 9/1993 | DeLonzor | 600/344 |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakely et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |
| 5,417,207 A | 5/1995 | Young et al. | |
| 5,421,329 A | 6/1995 | Casciani et al. | |
| 5,425,360 A | 6/1995 | Nelson | |
| 5,425,362 A | 6/1995 | Siker et al. | |
| 5,427,093 A | 6/1995 | Ogawa et al. | |
| 5,429,128 A | 7/1995 | Cadell et al. | |
| 5,429,129 A | 7/1995 | Lovejoy et al. | |
| 5,431,159 A | 7/1995 | Baker et al. | |
| 5,431,170 A | 7/1995 | Mathews | |

| Patent | Date | Name |
|---|---|---|
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A * | 4/1999 | Wang et al. .................. 600/344 |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A * | 7/1999 | Taylor et al. .................. 600/323 |
| 5,919,134 A | 7/1999 | Diab |
| 5,920,263 A | 7/1999 | Huttenhoff et al. |

| | | | | | | |
|---|---|---|---|---|---|---|
| 5,921,921 | A | 7/1999 | Potratz et al. | 6,181,959 B1 | 1/2001 | Schöllerman et al. |
| 5,922,607 | A | 7/1999 | Bernreuter | 6,184,521 B1 | 2/2001 | Coffin, IV et al. |
| 5,924,979 | A | 7/1999 | Swedlow et al. | 6,188,470 B1 | 2/2001 | Grace |
| 5,924,980 | A | 7/1999 | Coetzee | 6,192,260 B1 | 2/2001 | Chance |
| 5,924,982 | A | 7/1999 | Chin | 6,195,575 B1 | 2/2001 | Levinson |
| 5,924,985 | A | 7/1999 | Jones | 6,198,951 B1 | 3/2001 | Kosuda et al. |
| 5,934,277 | A | 8/1999 | Mortz | 6,206,830 B1 | 3/2001 | Diab et al. |
| 5,934,925 | A | 8/1999 | Tobler et al. | 6,213,952 B1 | 4/2001 | Finarov et al. |
| 5,940,182 | A | 8/1999 | Lepper, Jr. et al. | 6,217,523 B1 | 4/2001 | Amano et al. |
| 5,954,644 | A | 9/1999 | Dettling et al. | 6,222,189 B1 | 4/2001 | Misner et al. |
| 5,960,610 | A | 10/1999 | Levinson et al. | 6,226,539 B1 | 5/2001 | Potratz |
| 5,961,450 | A | 10/1999 | Merchant et al. | 6,226,540 B1 | 5/2001 | Bernreuter |
| 5,961,452 | A | 10/1999 | Chung et al. | 6,229,856 B1 | 5/2001 | Diab et al. |
| 5,964,701 | A | 10/1999 | Asada et al. | 6,230,035 B1 | 5/2001 | Aoyagi et al. |
| 5,971,930 | A | 10/1999 | Elghazzawi | 6,233,470 B1 | 5/2001 | Tsuchiya |
| 5,978,691 | A | 11/1999 | Mills | 6,236,871 B1 | 5/2001 | Tsuchiya |
| 5,978,693 | A | 11/1999 | Hamilton et al. | 6,236,872 B1 | 5/2001 | Diab et al. |
| 5,983,122 | A | 11/1999 | Jarman et al. | 6,240,305 B1 | 5/2001 | Tsuchiya |
| 5,987,343 | A | 11/1999 | Kinast | 6,253,097 B1 | 6/2001 | Aronow et al. |
| 5,991,648 | A | 11/1999 | Levin | 6,253,098 B1 | 6/2001 | Walker et al. |
| 5,995,855 | A | 11/1999 | Kiani et al. | 6,256,523 B1 | 7/2001 | Diab et al. |
| 5,995,856 | A | 11/1999 | Mannheimer et al. | 6,256,524 B1 | 7/2001 | Walker et al. |
| 5,995,858 | A | 11/1999 | Kinast | 6,261,236 B1 | 7/2001 | Grimblatov |
| 5,995,859 | A | 11/1999 | Takahashi | 6,263,221 B1 | 7/2001 | Chance et al. |
| 5,997,343 | A | 12/1999 | Mills et al. | 6,263,222 B1 | 7/2001 | Diab et al. |
| 5,999,834 | A | 12/1999 | Wang et al. | 6,263,223 B1 | 7/2001 | Sheperd et al. |
| 6,002,952 | A | 12/1999 | Diab et al. | 6,266,546 B1 | 7/2001 | Steuer et al. |
| 6,005,658 | A | 12/1999 | Kaluza et al. | 6,266,547 B1 | 7/2001 | Walker et al. |
| 6,006,120 | A | 12/1999 | Levin | 6,272,363 B1 | 8/2001 | Casciani et al. |
| 6,011,985 | A | 1/2000 | Athan et al. | 6,278,522 B1 | 8/2001 | Lepper, Jr. et al. |
| 6,011,986 | A | 1/2000 | Diab et al. | 6,280,213 B1 | 8/2001 | Tobler et al. |
| 6,014,576 | A | 1/2000 | Raley et al. | 6,280,381 B1 | 8/2001 | Malin et al. |
| 6,018,673 | A | 1/2000 | Chin et al. | 6,285,894 B1 | 9/2001 | Oppelt et al. |
| 6,018,674 | A | 1/2000 | Aronow | 6,285,895 B1 | 9/2001 | Ristolainen et al. |
| 6,022,321 | A | 2/2000 | Amano et al. | 6,285,896 B1 | 9/2001 | Tobler et al. |
| 6,023,541 | A | 2/2000 | Merchant et al. | 6,298,252 B1 | 10/2001 | Kovach et al. |
| 6,026,312 | A | 2/2000 | Shemwell et al. | 6,308,089 B1 | 10/2001 | Von der Ruhr et al. |
| 6,026,314 | A | 2/2000 | Amerov et al. | 6,321,100 B1 | 11/2001 | Parker |
| 6,031,603 | A | 2/2000 | Fine et al. | 6,330,468 B1 | 12/2001 | Scharf |
| 6,035,223 | A | 3/2000 | Baker, Jr. | 6,334,065 B1 | 12/2001 | Al-Ali et al. |
| 6,036,642 | A | 3/2000 | Diab et al. | 6,339,715 B1 | 1/2002 | Bahr et al. |
| 6,041,247 | A | 3/2000 | Weckstrom et al. | 6,343,223 B1 | 1/2002 | Chin et al. |
| 6,044,283 | A | 3/2000 | Fein et al. | 6,343,224 B1 | 1/2002 | Parker |
| 6,047,201 | A | 4/2000 | Jackson, III | 6,349,228 B1 | 2/2002 | Kiani et al. |
| 6,061,584 | A | 5/2000 | Lovejoy et al. | 6,351,658 B1 | 2/2002 | Middleman et al. |
| 6,064,898 | A | 5/2000 | Aldrich | 6,353,750 B1 | 3/2002 | Kimura et al. |
| 6,064,899 | A | 5/2000 | Fein et al. | 6,356,774 B1 | 3/2002 | Bernstein et al. |
| 6,067,462 | A | 5/2000 | Diab et al. | 6,360,113 B1 | 3/2002 | Dettling |
| 6,073,038 | A * | 6/2000 | Wang et al. ............. 600/323 | 6,360,114 B1 | 3/2002 | Diab et al. |
| 6,078,833 | A | 6/2000 | Hueber | 6,361,501 B1 | 3/2002 | Amano et al. |
| 6,081,735 | A | 6/2000 | Diab et al. | 6,363,269 B1 | 3/2002 | Hanna et al. |
| 6,081,742 | A | 6/2000 | Amano et al. | 6,370,408 B1 | 4/2002 | Merchant et al. |
| 6,083,157 | A | 7/2000 | Noller | 6,370,409 B1 | 4/2002 | Chung et al. |
| 6,083,172 | A | 7/2000 | Baker, Jr. et al. | 6,374,129 B1 | 4/2002 | Chin et al. |
| 6,088,607 | A | 7/2000 | Diab et al. | 6,377,829 B1 | 4/2002 | Al-Ali et al. |
| 6,094,592 | A | 7/2000 | Yorkey et al. | 6,381,479 B1 | 4/2002 | Norris |
| 6,095,974 | A | 8/2000 | Shemwell et al. | 6,381,480 B1 | 4/2002 | Stoddart et al. |
| 6,104,938 | A | 8/2000 | Huiku et al. | 6,385,471 B1 | 5/2002 | Mortz |
| 6,112,107 | A | 8/2000 | Hannula | 6,385,821 B1 | 5/2002 | Modgil et al. |
| 6,113,541 | A | 9/2000 | Dias et al. | 6,388,240 B2 | 5/2002 | Schulz et al. |
| 6,115,621 | A | 9/2000 | Chin | 6,393,310 B1 | 5/2002 | Kuenstner |
| 6,122,535 | A | 9/2000 | Kaestle et al. | 6,397,091 B2 | 5/2002 | Diab et al. |
| 6,133,994 | A | 10/2000 | Mathews et al. | 6,397,092 B1 | 5/2002 | Norris et al. |
| 6,135,952 | A | 10/2000 | Coetzee | 6,397,093 B1 | 5/2002 | Aldrich |
| 6,144,444 | A | 11/2000 | Haworth et al. | 6,400,971 B1 | 6/2002 | Finarov et al. |
| 6,144,867 | A | 11/2000 | Walker et al. | 6,400,972 B1 | 6/2002 | Fine |
| 6,144,868 | A | 11/2000 | Parker | 6,402,690 B1 | 6/2002 | Rhee et al. |
| 6,149,481 | A | 11/2000 | Wang et al. | 6,408,198 B1 | 6/2002 | Hanna et al. |
| 6,150,951 | A | 11/2000 | Olejniczak | 6,411,832 B1 | 6/2002 | Guthermann |
| 6,151,107 | A | 11/2000 | Schöllerman et al. | 6,411,833 B1 | 6/2002 | Baker, Jr. et al. |
| 6,151,518 | A | 11/2000 | Hayashi | 6,419,671 B1 | 7/2002 | Lemberg |
| 6,152,754 | A | 11/2000 | Gerhardt et al. | 6,421,549 B1 | 7/2002 | Jacques |
| 6,154,667 | A | 11/2000 | Miura et al. | 6,430,423 B2 | 8/2002 | DeLonzor et al. |
| 6,157,850 | A | 12/2000 | Diab et al. | 6,430,513 B1 | 8/2002 | Wang et al. |
| 6,163,715 | A | 12/2000 | Larsen et al. | 6,430,525 B1 | 8/2002 | Weber et al. |
| 6,165,005 | A | 12/2000 | Mills et al. | 6,434,408 B1 | 8/2002 | Heckel et al. |
| 6,173,196 | B1 | 1/2001 | Delonzor et al. | 6,438,399 B1 | 8/2002 | Kurth |
| 6,178,343 | B1 | 1/2001 | Bindszus et al. | 6,449,501 B1 | 9/2002 | Reuss |
| 6,181,958 | B1 | 1/2001 | Steuer et al. | 6,453,183 B1 | 9/2002 | Walker |

| | | |
|---|---|---|
| 6,453,184 B1 | 9/2002 | Hyogo et al. |
| 6,453,186 B1 * | 9/2002 | Lovejoy et al. ............... 600/386 |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 * | 2/2003 | Lovejoy et al. ............... 600/323 |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,815,218 B1 * | 11/2004 | Jacobson et al. ............... 438/1 |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |

| | | |
|---|---|---|
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,425 B2 | 9/2007 | Al-Ali |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,341,559 B2 | 3/2008 | Schulz et al. |
| 7,359,741 B2 | 4/2008 | Sarussi |
| 7,389,130 B2 * | 6/2008 | Delonzor et al. ............ 600/310 |
| 7,479,198 B2 * | 1/2009 | Guffrey et al. ............... 156/155 |
| 7,596,415 B2 * | 9/2009 | Brabec et al. ................ 607/121 |
| 7,936,111 B2 * | 5/2011 | Choi et al. ................... 310/339 |
| 7,947,148 B2 * | 5/2011 | Lahann et al. ............... 156/310 |
| 7,972,616 B2 * | 7/2011 | Dubrow et al. .............. 424/423 |
| 8,142,700 B2 * | 3/2012 | Sitti et al. ..................... 264/139 |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0092978 A1 * | 5/2003 | Fisher, III ..................... 600/391 |
| 2003/0100840 A1 | 5/2003 | Sugiura et al. |
| 2003/0109056 A1 * | 6/2003 | Vossmeyer et al. ........... 436/169 |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |

| | | |
|---|---|---|
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1* | 7/2004 | Al-Ali et al. ................. 600/323 |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0101848 A1 | 5/2005 | Al-Ali et al. |
| 2005/0113651 A1 | 5/2005 | Wood et al. |
| 2005/0175540 A1 | 8/2005 | Oraevsky et al. |
| 2005/0177034 A1 | 8/2005 | Beaumont |
| 2005/0197548 A1* | 9/2005 | Dietiker ........................ 600/323 |
| 2005/0228248 A1 | 10/2005 | Dietiker |
| 2005/0228299 A1 | 10/2005 | Banet |
| 2005/0277819 A1 | 12/2005 | Kiani et al. |
| 2005/0283059 A1 | 12/2005 | Iyer et al. |
| 2006/0020179 A1 | 1/2006 | Anderson et al. |
| 2006/0058594 A1 | 3/2006 | Ishizuka et al. |
| 2006/0068195 A1* | 3/2006 | Majumdar et al. ............ 428/323 |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0154063 A1* | 7/2006 | Fujihara et al. ............... 428/373 |
| 2006/0173247 A1* | 8/2006 | Medina ........................ 600/301 |
| 2006/0195028 A1 | 8/2006 | Hannula et al. |
| 2006/0200018 A1 | 9/2006 | Al-Ali |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276700 A1 | 12/2006 | O'Neil |
| 2007/0021659 A1 | 1/2007 | Delonzor et al. |
| 2007/0021660 A1 | 1/2007 | Delonzor et al. |
| 2007/0021662 A1* | 1/2007 | DeLonzor et al. ............ 600/344 |
| 2007/0027378 A1 | 2/2007 | Delonzor et al. |
| 2007/0027379 A1* | 2/2007 | Delonzor et al. ............ 600/344 |
| 2007/0027380 A1 | 2/2007 | Delonzar et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0078318 A1 | 4/2007 | Kling et al. |
| 2007/0100218 A1 | 5/2007 | Sweitzer et al. |
| 2007/0100219 A1 | 5/2007 | Sweitzer et al. |
| 2007/0117213 A1* | 5/2007 | Cole et al. ...................... 436/146 |
| 2007/0129622 A1 | 6/2007 | Bourget et al. |
| 2007/0200477 A1* | 8/2007 | Tuominen et al. ............ 313/309 |
| 2007/0218279 A1* | 9/2007 | Nonaka et al. ................ 428/365 |
| 2008/0009691 A1 | 1/2008 | Parker |
| 2008/0071154 A1 | 3/2008 | Hausmann et al. |
| 2008/0091089 A1 | 4/2008 | Guillory et al. |
| 2008/0091090 A1 | 4/2008 | Guillory et al. |
| 2008/0249393 A1 | 10/2008 | Finarov et al. |
| 2008/0316488 A1 | 12/2008 | Mao et al. |
| 2009/0040579 A1 | 2/2009 | Mickelson et al. |
| 2009/0087630 A1* | 4/2009 | Ward et al. .................... 428/206 |
| 2009/0134887 A1* | 5/2009 | Hu et al. ........................ 324/692 |
| 2009/0198117 A1* | 8/2009 | Cooper et al. ................. 600/347 |
| 2009/0278556 A1* | 11/2009 | Man et al. ...................... 324/693 |
| 2010/0013642 A1 | 1/2010 | Watson et al. |
| 2010/0016680 A1 | 1/2010 | Addison et al. |
| 2010/0017142 A1 | 1/2010 | Watson et al. |
| 2010/0081897 A1 | 4/2010 | Li et al. |
| 2010/0081899 A1 | 4/2010 | McKenna |
| 2010/0081901 A1 | 4/2010 | Buice et al. |
| 2010/0081902 A1 | 4/2010 | McKenna et al. |
| 2010/0090341 A1* | 4/2010 | Wan et al. ...................... 257/749 |
| 2010/0140160 A1* | 6/2010 | Dubrow et al. ............... 210/348 |
| 2010/0249554 A1 | 9/2010 | McKenna et al. |
| 2010/0249557 A1 | 9/2010 | Besko et al. |
| 2010/0261995 A1 | 10/2010 | McKenna et al. |
| 2010/0261996 A1 | 10/2010 | Li et al. |
| 2010/0285972 A1* | 11/2010 | Dubrow et al. ................ 506/7 |
| 2011/0066013 A1* | 3/2011 | Harrold ......................... 600/323 |
| 2011/0138610 A1* | 6/2011 | Choi et al. ..................... 29/596 |
| 2011/0192233 A1* | 8/2011 | Aizenberg et al. ............ 73/861 |
| 2011/0208103 A1* | 8/2011 | Leschinsky ................... 602/57 |
| 2011/0288386 A1* | 11/2011 | Taub ............................. 600/309 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| EP | 0724860 | 8/1996 |
| EP | 1986543 | 11/2008 |
| FR | 2685865 | 7/1993 |
| JP | 2111343 | 4/1990 |
| JP | 3116259 | 12/1991 |
| JP | 3116260 | 12/1991 |
| JP | 5049625 | 3/1993 |
| JP | 6014906 | 1/1994 |
| JP | 6269430 | 9/1994 |
| JP | 7001273 | 1/1995 |
| JP | 7236625 | 9/1995 |
| JP | 7246191 | 9/1995 |
| JP | 2000237170 | 9/2000 |
| JP | 3134144 | 2/2001 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9111137 | 8/1991 |
| WO | WO9502358 | 1/1995 |
| WO | WO9736536 | 10/1997 |
| WO | WO9857577 | 12/1998 |
| WO | WO9947039 | 9/1999 |
| WO | WO0028888 | 5/2000 |
| WO | WO0059374 | 10/2000 |
| WO | WO2005010567 | 2/2005 |
| WO | WO2005010568 | 2/2005 |
| WO | WO2007041331 | 4/2007 |

OTHER PUBLICATIONS

Endo et al, Potential Applications of Carbon Nanotubes, Springer-Verlag, Berlin, Heidelberg, 2008.*

Wilson et Al, Single-Wall Carbon Nanotube Conducting Probe Tips, Department of Physics, University of Warwick, Coventry, U.K., Jul. 22, 2002.*

Melechko et al., Synthesis of Vertically aligned Carbon Nanofibres for Interfacing with Live Systems, Materials Science and Engineering Department, North Carolina State University, Raleigh, North Carolina, IOP Publinsing Ltd, 2009.*

Melechko et al., Vertically Aligned Carbon Nanofibers and related Structures: Controlled Synthesis and Directed Assembly, Journal of Applied Physics, 1997.*

Bachtold et Al., Electrical Properties of Single Multiwalled Carbon Nanotubes, University Basel, 1999.*

Jung et al., Highly Adhesive, Transparent and Conductive Single-Walled Carbon Nanotube Film, IEEE, 2010.*

Ngo et al., Characteristics of Aligned Carbon Nanofibers for Interconnect Vi Applications, IEEE Electron Device Letters, vol. 27. No. 4, Apr. 2006.*

Sami Rosenblatt (Dissertation for PhD of Philosophy), Pushing the Limits of Carbon Nanotube Transistors, Cornell University, N.Y., Jan. 2006.*

Lee et al., An Optically-Driven Platform for Manipulation of Carbon Nanotubes, IEEE, 2009.*

Ben-Jacob et Al., Carbon Nanotube Micro-Electrodes for Neuronal Interfacing, Journal of Materials Chemistry, The Royal Society of Chemistry, 2008.*

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

http://www.fcw.com.my/fujifilm.html.

Ge et al., Carbon nanotube-based synthetic gecko tapes, PNAS, Jun. 26, 2007 vol. 104, No. 26, 10792-10795.

Mahdavi et al., A biodegradable and biocompatible gecko-inspired tissue adhesive, PNAS, Feb. 19, 2008 vol. 105, No. 7, 2307-2312.

Sethi et al., Gecko-Inspired Carbon Nanotube-Based Self-Cleaning Adhesives, Nano Letters, Feb. 12, 2008.

Yang et al., Converting Biomechanical Energy into Electricity by a Muscle-Movement-Driven Nanogenerator, Nano Letters, Feb. 9, 2009 vol. 9, No. 3, 1201-1205.

Yurdumankan et al., Origin of Higher Friction for Elastomers Sliding on Glassy Polymers, J. Phys. Chem. C. Dec. 10, 2006, 111, 960-965.

Yurdumankan et al., Synthetic gecko foot-hairs from multiwalled carbon nanotubes, ChemCommun., Jul. 5, 2005, 3799-3801.

* cited by examiner

NANOFIBER ADHESIVES USED IN MEDICAL DEVICES

BACKGROUND

The present disclosure relates generally to medical devices and methods, and more particularly to adhesives used with medical devices, such as sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present embodiments. Accordingly, it should be understood that these statements are to be read in this light, and not as admissions of prior art.

In medicine it is often desirable to attach materials to patient tissues, such as the skin, as part of the treatment process. For example, it may be desirable to use non-invasive techniques to continuously monitor a patient's physiological state. Such techniques may utilize data collected by a sensor, lead, or contact that is typically attached to the skin of the patient. For example, a patient's blood-, heart-, and/or brain-related data are often measured using various sensors placed on the patient for extended periods of time and relayed to some external monitor that can then be assessed by an appropriate healthcare professional. Typically, the sensors are held in place using conventional adhesive backings, such as those made from polymeric viscoelastic materials. After the patient no longer needs to be monitored, the sensors may be peeled from the patient's skin by overcoming the adhesive forces associated with the adhesive backing.

Despite the ubiquity of adhesive-backed sensors, relatively few advances have been made towards the mitigation of the discomfort associated with the peeling of the adhesive layer from the patient's skin while retaining strong adhesive properties. While this represents a mild annoyance for some, it can be a painful process for others who have sensitive skin, such as children, the elderly, those with allergies to various adhesive compositions, and those who have extended periods of stay in a healthcare facility.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to the use of nanofiber adhesives in medical devices. Such devices may include a sensor, such as for use with a patient monitoring system, having a layer of nanofiber adhesive. The nanofiber adhesive may be in a variety of forms and may be formed from different materials consistent with any number of desired properties. In one embodiment, the nanofiber adhesive may be formed from smaller subunits of nanotubes, which may adhere to various surfaces including patient tissue (e.g., skin). In other embodiments, the nanofiber adhesive may be formed from an array of nanofibers that are not made from smaller subunits, but are formed from a bulk material. In yet another embodiment the adhesive layer may be formed from a mixture of nanofibers formed from nanotubes and bulk materials. Due to the nature of the adhesive properties of the nanofiber layer, the removal of such a device from a patient may be a relatively painless process. Additionally, a device utilizing nanofiber adhesives may be further designed to allow monitoring of the adhesive state of the adhesive layer, thus enabling a user to determine attachment to a patient surface.

Figure 1:
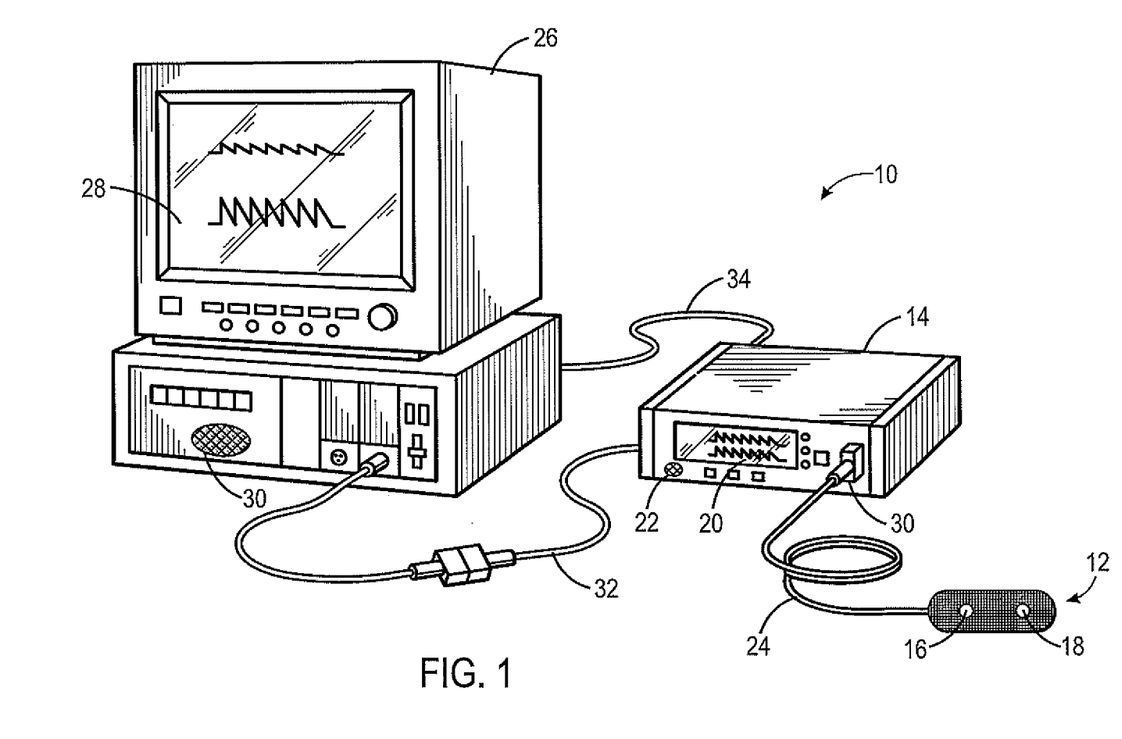
FIG. 1 is a perspective view of a patient monitoring system, in accordance with one aspect of the present disclosure.

With the foregoing comments in mind, a nanofiber adhesive as discussed herein may be used in various medical contexts, such as in the placement of different types of medical sensors, leads, or contacts on a patient. As may be appreciated, such sensors may be associated with monitoring systems for monitoring the sensors and processing data obtained via the sensors. By way of illustration, FIG. 1 is a perspective view of an embodiment of a pulse oximetry system 10. The system 10 includes a sensor 12 that includes a nanofiber adhesive and a pulse oximetry monitor 14. The sensor 12 may include an emitter 16 for emitting light at one or more wavelengths into a patient's tissue. A detector 18 may also be provided in the sensor 12 for detecting the light passing through or reflected by the tissue of a patient.

In one embodiment of the sensor 12, the emitter 16 and detector 18 may be on opposite sides of a digit such as a finger or toe, in which case the light that is emanating from the tissue has passed completely through the digit. However, in another embodiment of the sensor 12, the emitter 16 and detector 18 may be arranged so that light from the emitter 16 penetrates the tissue and is reflected by the tissue into the detector 18, such as a sensor designed to obtain pulse oximetry data from a patient's forehead. In one embodiment, the sensor 12 may be connected to and draw its power from the monitor 14 as shown. For example, the sensor 12 may be communicatively coupled to the monitor 14 via a cable 24 and connector 30.

The connector 30 of the sensor 12 may be engaged with a complimentary connector on the monitor 14.

The monitor 14 may be configured to calculate physiological parameters based on data received from the sensor 12 relating to light emission and detection. Further, the monitor 14 may include a display 20 configured to display the physiological parameters, other information about the system, and/or alarm indications. In the embodiment shown, the monitor 14 also includes a speaker 22 to provide an audible alarm in the event that the patient's physiological parameters are not within an expected range, as defined based on patient characteristics.

In the illustrated embodiment, the pulse oximetry system 10 also includes a multi-parameter patient monitor 26. The multi-parameter patient monitor 26 may be configured to calculate physiological parameters and to provide a central display 28 for information from the monitor 14 and from other medical monitoring devices or systems. For example, in one embodiment where the monitor 14 is a pulse oximetry monitor, the multiparameter patient monitor 26 may be configured to display a patient's oxygen saturation reading generated by the monitor 14, pulse rate information from the monitor 14, and/or blood pressure from a separate blood pressure monitor on the display 28. Additionally, the multi-parameter patient monitor 26 may emit a visible or audible alarm via the display 28 or a speaker 30, respectively, if the patient's physiological characteristics are found to be outside of the expected range. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations. The monitor 14 may be powered by a battery or by a conventional power source such as a wall outlet.

Figure 2:
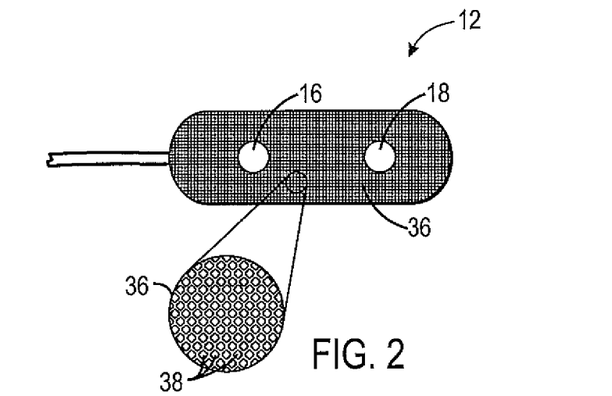
FIG. 2 depicts a sensor showing an adhesive layer, with a magnified view of the nanofibers which comprise the adhesive layer, in accordance with one aspect of the present disclosure.
Figure 3:
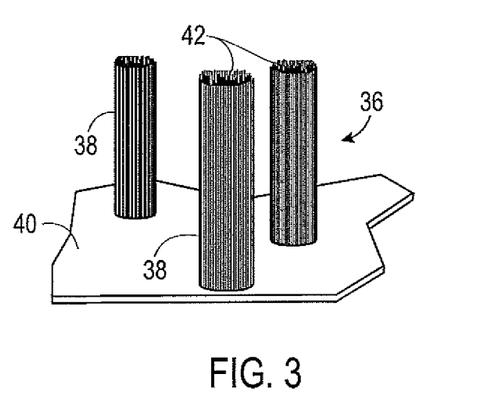
FIG. 3 is a magnified view of the nanofibers of FIG. 2, showing the individual nanotubes that comprise the nanofibers, in accordance with one aspect of the present disclosure.

As noted above, in one embodiment the sensor 12 may include a nanofiber adhesive, which may facilitate attachment of the sensor 12 to a patient. FIGS. 2 and 3 illustrate an embodiment of a sensor 12 having a layer 36 of nanofiber adhesive disposed on a backing layer 40 of the sensor 12. The shape and extent of the nanofiber adhesive layer 36 may vary to suit the type or function of sensor 12. That is, the nanofiber adhesive layer 36 may cover all or most of the patient contacting surface of the sensor 12 or may cover select portions of the sensor 12 (such as patterns, patches, strips, edges, and so forth) that provide sufficient surface area to supply the desired degree of adhesion, as discussed herein.

In one embodiment, the nanofiber adhesive layer 36 includes a population of nanofibers 38. In one embodiment, the nanofibers 38 of the adhesive layer 36 are composed of carbon. In other embodiments, the nanofiber materials may be composed of one or more of boron, silicon, boron carbide, silicon carbide, boron-silicon, cellulose and its synthetic analogs, collagen and its synthetic analogs, keratin and its synthetic analogs, or any suitable polymer.

The nanofiber adhesive layer 36 may be disposed on a backing layer 40 of the sensor 12 using a properly selected glue or polymeric bonding agent, such as poly(methylmethacrylate). In some embodiments, the bonding agent may be a combination of acrylate polymers or related compounds. In certain of these embodiments, the nanofiber adhesive layer 36 may be formed separately from the medical device on various surfaces including but not limited to metallic and/or semi-metallic catalyst substrates or beds, polymer matrices (such as a polymer film), and the like. The resulting bed, matrix, or other substrate of the nanofiber adhesive layer 36 may be glued or bonded to a backing layer 40 of the sensor body. Conversely, in one embodiment, the nanofiber adhesive layer may be bonded to the sensor body upon polymerization of a matrix of selected monomer or monomers, such as methyl methacrylate and related compounds. Thus, the polymer resulting from polymerization of the selected monomers bonds the nanofiber adhesive layer or population of nanofibers directly to the sensor body. In one embodiment, the sensor body may be made from any number of synthetic or natural polymeric materials that allow bonding by glues or viscoelastic adhesives.

Returning to FIG. 2 and, in particular, to the close-up of adhesive layer 36, in one embodiment the nanofibers 38 are aligned in a substantially parallel orientation with respect to one another and in a substantially perpendicular relation to the body of sensor 12. In one embodiment, the nanofibers 38 have a generally cylindrical or tapered cylindrical morphology and may have diameters in the range from about 100 nanometers (nm) to about 500 microns ($\mu$m) (e.g., between 100 nm and 1 $\mu$m, or between 0.8 $\mu$m to 3 $\mu$m, or between 50 $\mu$m and 500 $\mu$m). The diameters of the nanofibers 38 comprising the adhesive layer may be mono- or polydisperse.

FIG. 3 depicts a side view of a portion of the nanofiber adhesive layer 36 providing a closer view of nanofibers 38. In the embodiment shown, each nanofiber 38 is generally cylindrical, though the nanofibers may also have cross sections that are generally rectangular or rhomboidal. In some embodiments, the nanofibers may have cross sections (such as triangular cross sections) that result in morphologies resembling tapered pillars. In some embodiments, the nanofibers may be formed from a lithographic and/or etching process of an amorphous or patterned bulk material, such as a polymer or other material suitable for lithography or etching techniques. As depicted in FIG. 3, the nanofibers 38 may be formed from a tightly-packed bundle of nanotubes 42. The nanotubes 42 may be made from some or all of the materials previously listed with respect to nanofiber material composition.

The nanofibers 38 may be generated by a variety of processes including but not limited to: the formation of a superstructure such as a tightly packed bundle of nanotubes, fiber spinning of a solution or suspension of nanotubes, or a lithographic, etching, or similar process from a nanotube carpet or bulk polymer on a semi-metallic and/or metallic substrate or catalyst bed. Generally, the nanofibers 38 have lengths ranging from 100 nm to 500 $\mu$m. In one embodiment, the nanotubes 42 that form the nanofibers 38 have an average length of between 30 $\mu$m and 500 $\mu$m (e.g., between about 200 $\mu$m and about 500 $\mu$m) and are mono- or polydisperse. In one embodiment, the nanotubes 42 may have a diameter between 1 nm and 12 nm (e.g., between 2 nm and 8 nm or about 8 nm). The diameter of the nanotubes 42 may be mono- or polydisperse, or a combination of both with respect to the population of nanotubes 42. Further, in some embodiments the nanotubes 42 may be single-walled, double-walled, or multi-walled, or may be a combination of these wall configurations with respect to the population of nanotubes 42. In one embodiment, multi-walled nanotubes may contain between 3 and 8 walls, such as between 3 and 5 walls. Nanofibers 38 formed from bulk polymeric materials may have the same or different dimensions than the nanotubes 42 used to construct nanofibers 38. For example, the nanofibers 38 formed from bulk polymer materials may have lengths in the range of about 200 nm to about 500 nm.

In an embodiment, it may be desirable to use chemically-altered nanofibers, thus, in some embodiments, the nanotubes 42 may also be chemically functionalized or treated. Possible chemical methods for functionalization include, but are not limited to: acid-base chemistry, arylation chemistry, cycloaddition chemistry, diazonium chemistry, organometal chemistry, free-radical chemistry, vapor or gas chemistry, electrochemistry, and the like. In some embodiments, the functionalization of the nanotubes 42 may result in a chemical change of the sidewalls of some or all of the nanotubes 42 within a nanofiber 38. In one embodiment, the nanotubes 42 may be substantially functionalized at the patient contacting surface (i.e., the ends of the nanotubes 42) to alter their adhesive properties. In some embodiments, it may be desirable to chemically treat the formed nanofibers 38 instead of or in addition to the nanotubes 42 to alter their properties (e.g. in the case of nanofibers 38 formed from a bulk polymer). For example, the nanofibers 38 may be coated with a material to increase their adhesive capabilities. The material may include chemical functionalities that have an affinity for patient surfaces. For example, in one embodiment, the nanofibers 38 may be coated with oxidized dextran to increase interfacial adhesion strength.

Figure 4:
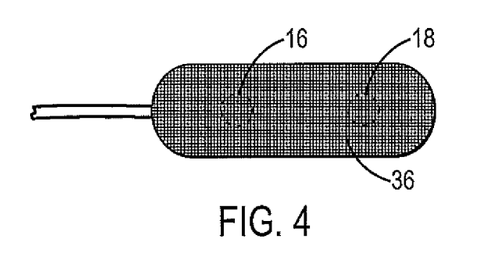
FIG. 4 is a view of an alternative embodiment of the sensor shown in FIG. 2, where the emitter and detector are covered by a nanofiber adhesive layer, in accordance with one aspect of the present disclosure.

In one embodiment, an emitter 16 and/or detector 18 of a sensor 12 are uncovered by the nanofiber adhesive layer 36 (as depicted in FIG. 2). In this embodiment, the nanofiber adhesive layer 36 may or may not be transparent to the wavelengths of light emitted and detected by the emitter 16 and detector 18. Turning to FIG. 4, in another embodiment one or both of the emitter 16 and detector 18 may be covered by the nanofiber adhesive layer 36. In such an embodiment, the composition of the nanofiber adhesive layer 36 may be selected so that the nanofiber adhesive layer 36 is generally transparent to the wavelengths of light that are to be emitted and detected.

Figure 5:
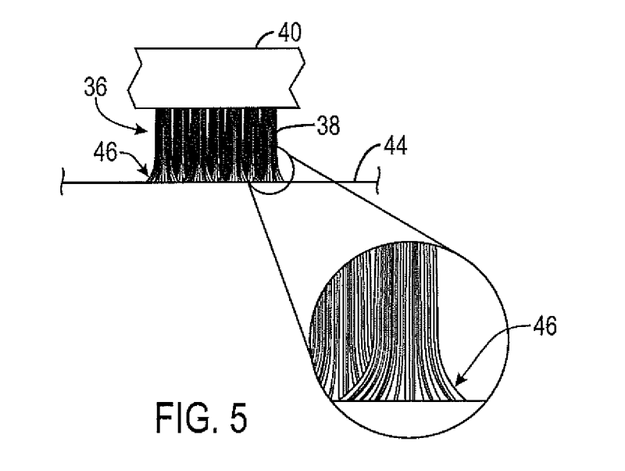
FIG. 5 is a side-on view of a mode of nanofiber adhesive layer adhesion to a patient surface, in accordance with one aspect of the present disclosure.

FIG. 5 represents a view of an embodiment of nanofiber adhesion to a patient's tissue 44. In one embodiment, the nanofibers 38 (and nanotubes 42 forming the nanofibers 38) adhere to the patient's tissue 44 by approaching the tissue at a given angle. In some embodiments, the angle of approach may be any angle between 0° and 90° (e.g., between 45° and 90° or about 90°). In one such embodiment, the nanofibers 38 and the nanotubes 42 that form the nanofibers 38 adhere to the patient tissue 44 via an end-on approach. In such an approach, upon contacting the patient surface 44, a downward force applied to "set" the nanofiber adhesive layer 36 deforms the ends 46 of the nanofibers, causing individual nanotubes 42 to splay outward, as depicted in the figure inset. The surface area of contact between the nanofibers 38 and the patient tissue 44 may therefore be greatly increased. In one such embodiment, van der Waals forces, usually responsible for intermolecular interactions, increase in proportion to the increased contact surface area, creating a strong force of attraction between the population of nanofibers 38 (and the nanotubes 42 forming the nanofibers 38) and the patient's tissue 44.

In further embodiments, the nanofibers 38 of the nanofiber adhesive layer 36 may also be arranged in such a way such that in addition to van der Waals forces, the nanofiber adhesive layer 36 may also have an adhesive component arising from capillary forces. For example, a nanofiber adhesive layer 36 of a properly selected nanofiber 38 material may be arranged in such a way and with such dimensions as to allow water to be taken up by capillary forces, thereby allowing adhesion to wet patient surfaces, such as internal tissues or wet skin. Thus, the nanofiber adhesive layer 36 may be used not only on dry patient skin, but any patient tissue 44 where an increased interfacial contact is attainable.

In one embodiment, the nanofiber adhesive layer 36 can be removed by peeling the sensor 12 from the tissue 44 at an angle such that the energy of detachment is reduced or minimized. For example, the relationship between the peeling angle and the energy of detachment may be represented by the equation:

$$G = \frac{F(1 - \cos\theta)}{w} \quad (1)$$

where G is the energy of detachment, F is the peeling force, w is the width of the adhesive layer 36, and θ is the angle that the adhesive layer 36 is peeled back for all angles greater than or equal to 45° (other variables may play a role at lower angles, such that the energy of detachment may also depend on the elastic stiffness of the adhesive layer, the weight of the sensor, and the like). In accordance with equation (1), the energy of detachment of a given sensor from a standard surface (e.g., the patient's tissue 44) is determined by the peeling angle θ, where the force used to remove the adhesive layer 36 has a minimum value at a given angle (such as 45° in one embodiment). Thus, by removing the adhesive layer 36 (and attached medical device, such as sensor 12) at a suitable peeling angle θ, detachment energy may be reduced or minimized, thereby reducing patient discomfort.

Figure 6:
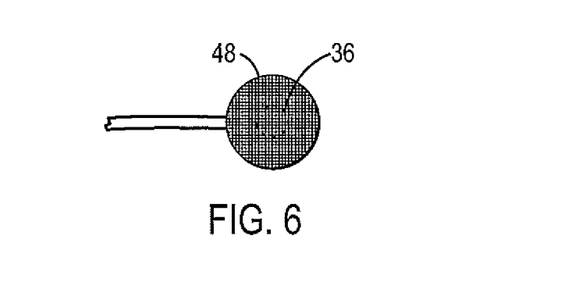
FIG. 6 depicts a non-pulse oximetry sensor, such as an EEG or ECG sensor, in accordance with one aspect of the present disclosure.

As will be appreciated, a nanofiber adhesive layer 36 may be provided on various types of medical devices in addition to the spectrophotometric sensor 12 discussed above. For example, FIG. 6 illustrates a plan view of an embodiment of a nanofiber adhesive layer 36 disposed on an EEG or ECG lead 48. In one embodiment, a patient-contacting surface of the lead 48 is covered, partially or completely, by a nanofiber adhesive layer 36. As discussed above, the nanofiber adhesive layer 36 may be disposed on a non-conductive backing material of the lead 48 such that, when the adhesive layer 36 is contacted to a patient's tissue, the lead 48 becomes adhered to the patient. While sensors and leads, such as those discussed above, represent certain types of medical devices on which a nanofiber adhesive layer 36 may be employed to adhere all or part of a medical device to a patient, any type of medical device that is adhered or attached to a patent may benefit from the use of a nanofiber adhesive layer 36. For example, bandages, wraps, dressings, portable monitoring devices, and so forth may also benefit from the addition of a nanofiber adhesive layer 36 as discussed herein.

Figure 7:
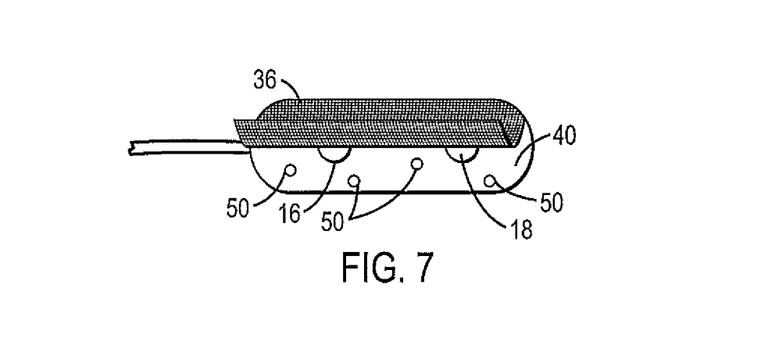
FIG. 7 is a sensor, where the adhesive layer has been pulled back to reveal electrical contacts, in accordance with one aspect of the present disclosure.

Turning now to FIG. 7, a peel-away view of an embodiment of a medical device (provided as a sensor 12) with a nanofiber adhesive layer 36 is depicted. In the depicted view, at least two electrical contacts 50 capable of conducting a current modulated by the state of the adhesive layer 36 are disposed on the device body. In one embodiment, the electrical contacts 50 are made from a metal such as copper, gold, silver, aluminum, and the like, though the electrical contacts may be made from any suitable conductive material or composition or any combination of the above. In one embodiment, a current between the electrical contacts 50 may be responsive to or indicative of the adhesive state of the adhesive layer 36. For example, the adhesive state may be represented by a binary function wherein the sensor is attached to the patient's tissue 44 in one state and unattached in the other state. Therefore, a characteristic of the current carried (or not carried) between the electrical contacts 50 may be evaluated or measured to determine whether the sensor is "on" or "off", i.e., adhered or not adhered.

For example, in one embodiment, the electrical contacts 50 may be electrically isolated from one another when the nanofiber adhesive layer 36 is not applied to a patient, i.e., no current flows between the electrical contacts when the sensor 12 is not adhered to a patient. Such a non-conductive state may signify that the sensor 12 is not applied, i.e., is "off". Upon contacting a patient's tissue, a basic electrical circuit may result wherein an electrical current is able to pass between the electrical contacts 50. Such a circuit may result from the current passing through the patient skin or tissue in contact with the nanofibers 38 of the adhesive layer 36 or may pass through the adhesive layer 36 itself in response to a conformational change in the nanofibers 38 associated with adhesion. Such a state of positive conductivity may signify that the sensor 12 is applied, i.e., is "on".

In another embodiment, the electrical contacts 50 may not be electrically isolated. Instead, an electrical current may be capable of passing between the electrical contacts 50 through the continuous structure of the nanofiber adhesive layer 36, so that some amount of current flows between the electrical contacts 50 regardless of the application state of the sensor. In such an embodiment, a characteristic (such as the measured current or voltage) of the flow of current between the electrical contacts 50 may vary when the sensor 12 is adhered to a patient as compared to when the sensor 12 is not applied to the patient. In such an embodiment, the value and/or variation of the varying characteristic may be utilized to determine the adhesion state of the sensor 12. While the preceding describes an example in which conductive characteristics of a nanofiber adhesive layer 36 may be used to determine whether a sensor 12 is applied to a patient, it should be appreciated that such conductive characteristics may be used to evaluate the adhesive state of a nanofiber adhesive layer 36 in other contexts, including non-medical contexts.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may be applied to measurements of blood oxygen saturation as well as other physiological measurements. Rather, the various embodiments may cover all modifications, equivalents, and alternatives falling within the spirit and scope of the disclosure as defined by the following appended claims.

What is claimed is:

1. A device, comprising:
   a backing layer;
   an adhesive layer comprising a plurality of nanofibers attached to the backing layer to couple the device to a patient tissue; and
   two or more electrical contacts positioned within or beneath the adhesive layer, wherein the two or more electrical contacts are capable of conducting a current through the adhesive layer or through the patient tissue to provide a signal related to an adhesive state of the adhesive layer.

2. The device of claim 1, wherein the plurality of nanofibers of the adhesive layer undergo a conformational change when adhered to the substrate such that a characteristic of the current flowing between the two or more electrical contacts is altered.

3. The device of claim 1, wherein the electrical contacts are positioned within the adhesive layer.

4. The device of claim 1, wherein the device comprises a pulse oximetry sensor, electroencephalogram lead, or an electrocardiogram lead.

5. A medical device, comprising:
   a backing material;
   a sensor or lead attached to the backing material, wherein the sensor or lead is capable of generating physiological data monitored by a patient monitor;
   an adhesive layer comprising a plurality of nanofibers configured to adhere the medical device to a patient tissue, wherein the adhesive layer is attached to the backing material; and
   two or more electrical contacts configured to conduct a current through the adhesive layer or through the patient tissue to provide a signal related to an adhesive state of the adhesive layer.

6. The medical device of claim 5, wherein the plurality of nanofibers are aligned substantially perpendicular to the backing layer.

7. The medical device of claim 5, wherein the adhesive layer is attached to the backing material using a glue or a polymeric bonding agent.

8. The medical device of claim 5, wherein the plurality of nanofibers comprise a polymer material.

9. The medical device of claim 5, wherein the plurality of nanofibers are comprised of any one of or a combination of single, double, or multiwalled carbon nanotubes.

10. The medical device of claim 5, wherein the medical device comprises a pulse oximetry sensor, an electroencephalogram lead, or an electrocardiogram lead.

11. The medical device of claim 5, wherein the plurality of nanofibers comprise one or more of carbon, boron, silicon, boron carbide, silicon carbide, boron-silicon, cellulose or its synthetic analogs, collagen or its synthetic analogs, or keratin or its synthetic analogs.

12. A method of manufacturing a medical device, comprising:
   applying a sensor or lead on a backing material;
   applying an adhesive layer on the backing material, wherein the adhesive layer comprises a plurality of nanofibers configured to adhere the medical device to a patient tissue; and
   applying electrical contacts between the backing material and the adhesive layer, or within the adhesive layer, to provide a signal related to an adhesive state of the adhesive layer.

13. The method as recited in claim 12, wherein the plurality of nanofibers are disposed in a general parallel orientation in relation to one another and are substantially perpendicular in relation to the backing material.

14. The method as recited in claim 12, wherein the plurality of nanofibers comprise carbon nanotubes.

15. The method as recited in claim 12, comprising forming the plurality of nanofibers by performing a lithographic or etching process on a bulk polymer.

16. The method as recited in claim 12, wherein the plurality of nanofibers comprise one or more of carbon, boron, silicon, boron carbide, silicon carbide, boron-silicon, cellulose and its synthetic analogs, collagen and its synthetic analogs, keratin and its synthetic analogs, or a polymer.

17. The medical device of claim 12, comprising chemically altering some or all of the plurality of nanofibers by coating or chemically functionalizing the respective nanofibers.

18. The method of claim 12, wherein applying the adhesive layer on the backing material comprises gluing or bonding the adhesive layer to the backing material.

* * * * *